United States Patent [19]

Hughes

[11] Patent Number: 4,458,061

[45] Date of Patent: Jul. 3, 1984

[54] 9-THIABICYCLONONANEDIISOCYANATES AND POLYMERS MADE THEREFROM

[75] Inventor: David W. Hughes, Midland, Mich.

[73] Assignee: The Dow Chemical Company, Midland, Mich.

[21] Appl. No.: 426,550

[22] Filed: Sep. 29, 1982

[51] Int. Cl.³ .............................................. C08G 18/77
[52] U.S. Cl. ........................................ 528/73; 549/9; 549/23; 549/49
[58] Field of Search .................. 528/73; 549/9, 23, 49

[56] References Cited

U.S. PATENT DOCUMENTS

| | | | |
|---|---|---|---|
| 2,729,618 | 1/1956 | Mueller et al. | 260/75 |
| 3,248,373 | 4/1966 | Barringer | 260/77.5 |
| 3,644,415 | 2/1972 | Weil et al. | 260/327 |

FOREIGN PATENT DOCUMENTS 1061472  3/1967  United Kingdom .
1061473  3/1967  United Kingdom .

OTHER PUBLICATIONS

*Aspects of Homogeneous Catalysis*, vol. 2, Chapter 3, pp. 78–82, 100, 101 & 111–117, 1972, Heimbach.
Chemical Abstracts 84:121,245b, Dzhemilev et al.
Journal of Organic Chemistry 31 (6), pp. 1669–1679, (1966), Weil et al.
Journal of Organic Chemistry 31 (6), pp. 1663–1668, (1966), Corey et al.
Journal of Organic Chemistry, USSR, 16 (7), pp. 1210–1218, (1980), Tolstikov et al.

*Primary Examiner*—H. S. Cockeram
*Attorney, Agent, or Firm*—Charles J. Enright

[57] ABSTRACT

Novel monomers of the structure:

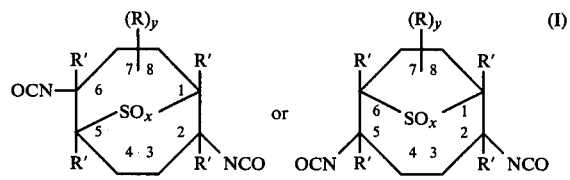

wherein each R, which may be the same or different, is an alkyl group containing 1 to 3 carbon atoms; each R', which may be the same or different, is hydrogen or methyl, at least two R' are hydrogen; and x and y are independently 0, 1 or 2, are made and used to produce polyurethanes, polyureas and other useful polymers.

32 Claims, No Drawings

9-THIABICYCLONONANEDIISOCYANATES AND POLYMERS MADE THEREFROM

BACKGROUND OF THE INVENTION

This invention relates to novel 9-thiabicyclononanediisocyanates which have utility as monomers in making polyurethanes and other polymers.

A polymer is a large molecule built up by the repetition of small, simple chemical units called monomers. The character of the monomer unit has a strong effect on the physical and chemical properties of the polymer. For example, it is common to incorporate a para-phenylene group into a monomer to add rigidity to the polymer chain. This can engender desirable properties in the polymer such as: raising the melting point, increasing the stress/strain property ratios and improving the heat distortion performance.

The incorporation of aromatic nuclei in polymer chains, however, has its drawbacks. Polymers containing aromatic nuclei are susceptible to deterioration. They may stiffen and become brittle, change color, or yellow and weaken. Opaque fillers, light stabilizers and antioxidants are added to alleviate these problems. Aliphatic monomers yield polymers which are less susceptible to degradation but do not impart the same rigidity.

OBJECTS OF THE INVENTION

It is an object of this invention to provide a monomer unit which will impart improved properties to a polymer chain. It is also an object of this invention to provide a use for 9-thiabicyclononanediisocyanates comprising incorporating them into a polymer.

SUMMARY OF THE INVENTION

These and other objects of the invention are effected by a monomer of the formula:

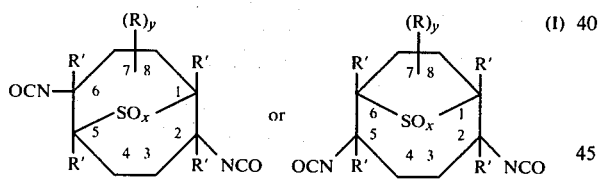

wherein each R which may be the same or different is an alkyl group containing 1 to 3 carbon atoms; each R' which may be the same or different is hydrogen or methyl, at least two R' are hydrogen; y is 0, 1 or 2 and x is 0, 1 or 2.

Incorporation of these monomers into a polyurethane or other polymer chain induces chain rigidity as evidenced by stress/strain properties and phase change properties. It is presumed that the sulfur bridge is responsible for decreasing the degrees of freedom in the molecule and thus imparting stiffening to the polymer chain.

DETAILED DESCRIPTION OF THE INVENTION

Preparation of the thiabicyclononanes starts with $C_4$-$C_8$ di-unsaturated hydrocarbons. Examples of such hydrocarbons include butadiene, piperylene or 1,3-pentadiene; 1,3-hexadiene; 1,3-heptadiene; 5-methyl-1,3-hexadiene; isoprene; and 3-methyl-1,3-pentadiene. The starting dienes may be used singly or a mixture of starting dienes may be used. The starting materials may be represented by the formula:

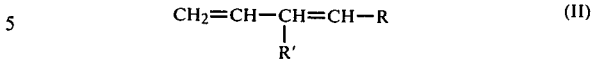

wherein R and R' are as defined above. Examples of R are hydrogen, methyl, ethyl, n-propyl and isopropyl. Preferably R is methyl. R' is preferably hydrogen. Piperylene is a preferred diene.

The dienes II are cyclodimerized to form a 1,5-cyclooctadiene III.

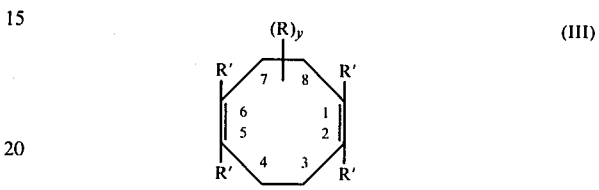

Cyclodimerization of the diene is a known reaction. Examples of this reaction can be found at J. A. Berson et al., JACS, 98 (19), pp. 5937–68 (1976) (Chem. Abstr. 86:70,9559); and U. M. Dzhemilev et al., Neftekhimiya, 15 (6), pp. 819–24 (1975) (Chem. Abstr. 84:121,2456); all of which are incorporated herein by reference.

A preferred method of conducting the cyclodimerization of piperylene is by heating and stirring a mixture of piperylene in other hydrocarbons with a catalyst containing an iron(III)salt, a trialkyl aluminum compound and a chelating nitrogen ligand.

These processes yield varying amounts of the following isomers when the R group is methyl and y is 2.

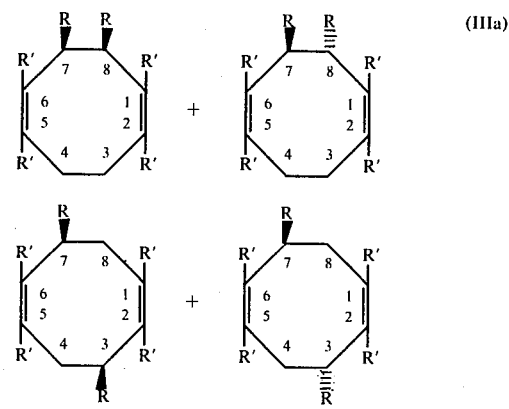

These isomers as well as isomers where y is 0 or 1 and R' is $CH_3$, are collectively included in the definition of the cyclooctadienes III. Note that the R groups are as defined above and are not attached to the carbons of the double bond. The double bonds are positioned between the 1 and 2 carbons and between the 5 and 6 carbons. The R groups may be attached only to the 3, 4, 7 and 8 carbons. When y is 0 and R is H, there is a single unsubstituted cyclooctadiene. When R' is methyl, that group is attached to a carbon of the double bond. While the R' methyl may be attached to carbons 1, 2, 5 or 6, only two R' may be methyl.

The cyclooctadienes III may be converted to thiabicyclononanes IV by the reaction disclosed in Weil et al. in J. Org. Chem., 31 (6), pp. 1669–1679 (1966); or Corey et al. in J. Org. Chem., 31 (6), pp. 1663–1668 (1966); or Tolstikov et al. in Zh. Org. Khim., 16 (7), pp. 1408–1418 (1980) or British Pat. Nos. 1,061,472 and 1,061,473; all of which are incorporated herein by reference.

These references teach that a cyclooctadiene III may be converted to the thiabicyclononane dichloride IV by treatment with sulfur dichloride. This yields

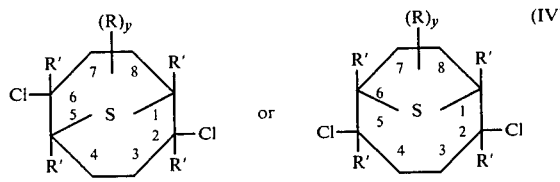

where R, R' and y are as defined in I and the R groups may be connected to the 3, 4, 7 or 8 ring carbons, but not the carbons directly attached to either the sulfur or chlorine atoms. The chlorine atoms are not attached to vicinal carbon atoms. The term TBCN is used hereinafter to describe generically the 9-thiabicyclononane IV, divalent radical without the chlorine atoms, which may be derived from the generic cyclooctadiene III.

Either or both of the [3.3.1] and [4.2.1] structures are found in the product as it has been found that the two structures are interconvertible during any reaction, even by merely dissolving in an ionizing solvent.

The preparation of the TBCN dichloride IV is accomplished by reacting the corresponding cyclooctadiene III with sulfur dichloride or other sulfur chloride. This is most conveniently done in the liquid phase, although it can also be accomplished in the vapor phase. The reaction is exothermic and, therefore, the reactants should be admixed by slow addition of one to the other, or, preferably, of both to a mutual solvent. Suitable solvents are any that are substantially inert to sulfur dichloride or the sulfur chloride and cyclooctadiene. Illustrative examples of suitable solvents include hydrocarbons such as toluene, benzene, hexane, cyclohexane, mineral spirits, chlorocarbons such as methylene chloride, carbon tetrachloride, ethylene dichloride, trichloroethylene, perchloroethylene, chlorobenzene, ethers such as diethyl ether, or miscellaneous solvents such as carbon disulfide, thionyl chloride, acetic anhydride, acetyl chloride, nitromethane, nitrobenzene, and dimethyl formamide.

The reaction temperature is from $-40°$ C. to $150°$ C., however, the preferred range is between $-20°$ C. and $100°$ C. It is particularly convenient to employ reaction temperatures near ambient temperature, and to cool the reaction by water-jacketing the reactor using water, also at ambient temperature.

The reaction is very rapid and generally is complete within a few seconds to a few hours after the reactants are admixed, depending on temperature. Therefore, a catalyst is not necessary. Nonetheless, if desired, the reaction may be catalyzed by addition of Lewis acids (e.g., $FeCl_3$), iodine, light or peroxides.

While sulfur dichloride is the preferred reactant, sulfur monochloride may be employed to obtain the TBCN dichlorides; however, the use of sulfur monochloride results in a more complex reaction mixture which entails troublesome purification steps. Sulfur tetrachloride may also be used, with resultant formation of some TBCN having more than two chlorine atoms per molecule.

A preferred method of making the TBCN dichloride is by admitting separate streams of the corresponding cyclooctadiene III and sulfur dichloride, each dissolved in an appropriate solvent into a line containing a static mixer. The concentrations of the feed solutions and the ratio in which they are admitted into the reactor are controlled to ensure a slight molar excess of sulfur dichloride. The line is cooled to ensure a maximum reactor temperature of $-5°$ C. Preferably the sulfur dichloride is stabilized according to the method described in U.S. Pat. No. 3,071,441 which is incorporated herein by reference.

The 9-oxides or 9,9-dioxides, i.e., where x is 1 or 2 are prepared by the oxidation of the corresponding sulfide. Prior to oxidation, the chlorine atoms should be replaced by the isocyanate groups as described herein. Illustrative oxidizing agents include hydrogen peroxide, peracetic acid, perbenzoic acid, perphthalic acid or other peroxy organic acids; nitric acid; nitrogen dioxide or tetraoxide; permanganates; chromic acid or dichromates; bromic acid or bromates; hypochlorous acid or hypochlorites; and ozone or molecular oxygen (preferably using a catalyst such as vanadium oxide or nitrogen dioxide).

The TBCN dichlorides may be converted to the TBCN diisocyanate by known means. Exemplary means include treating the TBCN dichloride with a cyanate salt. For example, the TBCN dichloride may be reacted with potassium cyanate in acetonitrile at room temperature. Preferred cyanate salts are sodium, potassium or ammonium cyanate. A phase-transfer catalyst is recommended when using sodium cyanate.

The dimethyl TBCN diisocyanate isomer mixture, where $y=2$ and $R=CH_3$, is a liquid at room temperature. This improves the processability of the compound over the unsubstituted TBCN diisocyanate, where $y=0$, which melts at about $71°$ C.–$72.5°$ C. The dimethyl TBCN diisocyanate isomer mixture may be pumped into a liquid system whereas the unsubstituted material must be melted or dissolved to be pumped. Accordingly, the dimethyl TBCN diisocyanate isomer mixture is preferred.

The TBCN diisocyanates of the invention may be used to form polyurethane polymers and polyurethane urea polymers, polyureas, polyurethane isocyanurates, polyurea isocyanurates and polyisocyanurates by step reaction polymerization.

In polymers the TBCN diamine monomer unit has the formula:

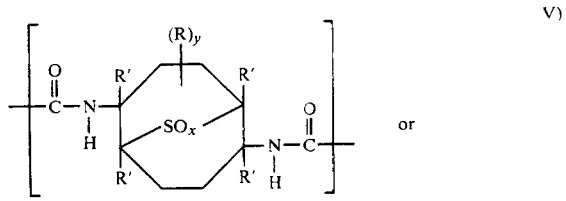

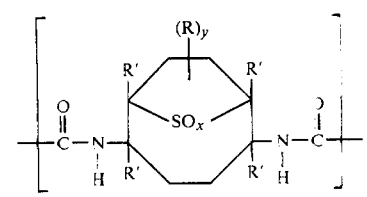

wherein R, R', x and y have their earlier mentioned definitions and positions.

The polyisocyanurates contain a trifunctional trimer unit which contains three TBCN units. The structure is:

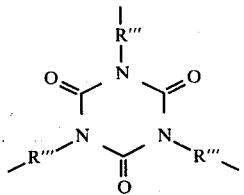
(VI)

wherein R''' is

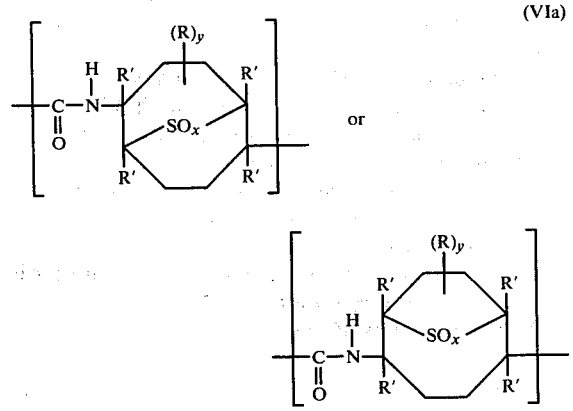
(VIa)

and R, R', x and y have their above-defined meanings.

Accordingly the invention also comprises a method for making a polymer wherein a characterizing amount of monomer units of the above formulae are incorporated. By characterizing amount it is meant a sufficient amount of the TBCN monomer units V are present in the polymer so that the polymer exhibits properties resulting from the presence of the TBCN monomer V. Preferably the polymer contains at least 0.5 mole percent of the monomer units V and more preferably at least about 10 mole percent and even more preferably at least about 40 mole percent of the monomer units V.

The polyurethanes of the invention may have the following structure:

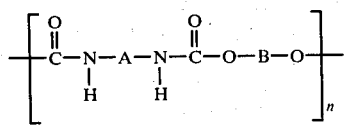
(VII)

wherein A is TBCN; B is a divalent hydrocarbon radical and n is the number of monomer units in the polymer. Preferably, B is an aliphatic hydrocarbon chain such as ethylene, n-propylene, n-butylene, etc.

The polymer VII may be formed by contacting the TBCN diisocyanate I with a polyol HO-B-OH such as ethylene glycol, 1,4-butanediol, . . . hydroxy-terminated polymers and copolymers of ethylene glycol and propylene glycol, or any of the materials referred to in the trade as polyols, such as hydroxy-terminated copolymers of ethylene glycol and propylene glycol initiated on sucrose or glycerine, or hydroxy-terminated polyesters (either di- or higher hydroxy functionalized), or any mixtures of such materials. Known techniques may be used.

The polyureas of the invention may have the structure:

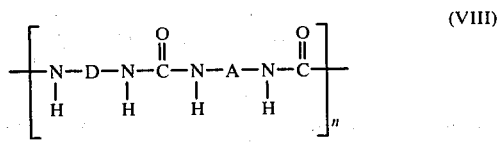
(VIII)

wherein A is TBCN; D is a divalent hydrocarbon radical and n is the number of monomer units in the polymer. Preferably, D is an aliphatic hydrocarbon chain such as ethylene, n-propylene, n-butylene, etc.

The polymer VIII may be formed by contacting the TBCN diisocyanate I with a polyamine $H_2N$—D—$NH_2$ such as 1,4-diaminobutane, ethylene diamine or its oligomers, 1,6-hexanediamine, 1,4-cyclohexanediamine, piperazine, N-(2-aminoethyl)-piperazine, amine-terminated homopolymers and copolymers of ethylene glycol and propylene glycol (either di- or higher amine functionalized), 2,4-diaminotoluene, 2,5-diaminotoluene, 2,6-diaminotoluene, methylene di(phenylamine), or 2,7-diaminofluorene. Known techniques may be used. Because the TBCN diisocyanates I are aliphatic diisocyanates, the reaction of I and the polyamine is slower than often encountered in making polyureas using aromatic diisocyanates, enabling the preparation of such polyureas.

Other polymers may be made by reaction of the TBCN diisocyanates I with diacids, amino-alcohols and dimercaptans.

The polymers formed with the above-described monomer units have utility as coatings, films and castings. Surprisingly, such polymers exhibit properties superior to those in which aromatic groups have been incorporated into the polymer backbone.

EXAMPLE 1

Preparation of Dimethyl 1,5-Cyclooctadiene (III)

20 Ml (100 mmoles) of 50 percent piperylene in other $C_5$ hydrocarbons, 10 ml of toluene, 0.19 g (0.5 mmole) of tris(2,4-pentanedionato-O,O')-iron (also known as iron tri(acetylacetonate), CA registry number [14024-18-1]) and 0.3 g (1.0 mmole) of N,N'-(1,2-dimethyl-1,2-ethanediylidene)bis[4-methoxy-benzenamine] (CA registry [19215-52-2]) are combined under nitrogen in a 50-ml three-necked flask equipped with reflux condenser and nitrogen inlet. The mixture is stirred magnetically and heated to 55° C. 1.5 ml of triisobutyl aluminum (1.0M in toluene—1.5 mmoles) is added. A sample is taken after 1.6 hours and analyzed by gas chromatography. Piperylene is 90 percent converted. The dimethyl cyclooctadiene yield is 71 percent based on converted piperylene. In this embodiment R is methyl, R' is hydrogen and y is 2.

EXAMPLE 2

Preparation of Dimethyl TBCN Dichloride

In this embodiment, R is methyl, R' is hydrogen and y is 2. The cyclooctadiene of Example 1 may be used as the starting material. This example describes a continuous process setup. The reactor used is a static inline mixer which is jacketed. A 50:50 by volume mixture of ethylene glycol and water at −30° C. is circulated through the jacket. Separate inlets are provided ahead of the reaction zone for cyclooctadiene and sulfur dichloride reactant solutions. An outlet valve is provided after the reaction zone to remove products.

850 ml of dimethyl-1,5-cyclooctadiene (730 g, 5.36 moles DMCOD) containing about 12 percent other piperylene dimers is mixed with 175 ml of methylene chloride and connected to one inlet. 355 ml of sulfur dichloride (575 g, 5.58 moles) dissolved in 3600 ml of methylene chloride is attached to the second inlet.

Both reactants are fed to the reactor simultaneously. The DMCOD solution is fed at about 45 ml/min. The sulfur dichloride solution is fed at about 172 ml/min. The feeds are exhausted in about 23 minutes. During the reaction time the temperature inside the reaction zone rises 11° C. Products are removed from the reaction zone at the same rate that they are added. When the feeds are exhausted the reactor zone is flushed with methylene chloride. The methylene chloride is evaporated from the product to give a black oil. Distillation of this oil at 85° C.-95° C. and 0.05–0.1 mm Hg gives about 1100 g of a very light yellow oil. Infrared and nuclear magnetic resonance spectra are consistent with a mixture of dimethyl TBCN dichloride isomers.

EXAMPLE 3

Preparation of Dimethyl TBCN Diisocyanate

A 5000-ml three-necked flask equipped with nitrogen inlet/outlet, reflux condenser, thermometer, and mechanical stirrer is dried at 150° C. for 1 hour and flushed with nitrogen. To this flask is charged 382.8 g of 97.8 percent potassium cyanate (4.612 moles) 538.23 g of distilled dimethyl-dichloro-9-thiabicyclononanes (2.25 moles) and 3000 ml of acetonitrile. This mixture is stirred and heated to reflux for 3 hours. A sample taken after 3 hours shows a strong absorption for isocyanate by infrared spectroscopy (2250 cm$^{-1}$). Nuclear magnetic resonance spectroscopy indicates the reaction is complete. The reaction mixture is filtered, rotary evaporated and the residue extracted with methylene chloride. After filtration and rotary evaporation, a light yellow oil is obtained which is distilled at about 130° C., 0.10 mm Hg to give about 470 g of a colorless oil. This oil contains about 33.24 percent NCO (theory, 33.30 percent) as determined by ASTM Method D-2572.

EXAMPLE 4

Polyurethane Made With Dimethyl TBCN Diisocyanate 60.00 g of Voranol®4702 (a high MW triol) available from The Dow Chemical Company and 19.67 g of 1,4-butane diol are mixed together. 62.71 g of dimethyl-9-thiabicyclononane diisocyanate is added to this mixture and stirred, care being taken to avoid air entrapment. 1.42 g of dibutyltin dilaurate are added, quickly mixed in, and the formulation is quickly poured into a 6"×6"×⅛" steel window mold treated with a mold release agent. The mold is then placed in an oven for curing at 120° C.-122° C. for 1.5 hours. The resulting clear cast polyurethane specimen exhibits tensile strength of 2945 psi and 180 percent elongation at break, versus 1958 psi and 55 percent elongation for a similar formulation made with carbodiimide-modified MDI.

It is to be understood that the foregoing examples are illustrative in nature and are not to be construed in a limiting sense. The embodiments of the invention in which an exclusive property or privilege is claimed is limited only by the scope of the hereinafter appended claims.

What is claimed is:

1. A monomer of the formula:

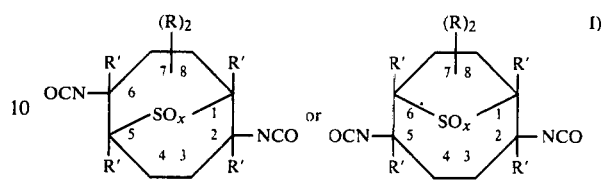

wherein each R, which may be the same or different, is an alkyl group containing 1 to 3 carbon atoms; each R', which may be the same or different, is hydrogen or methyl, at least two R' are hydrogen; and x 0, 1 or 2.

2. The monomer of claim 1 wherein all R' are hydrogen.

3. The monomer of claim 2 wherein x is zero.

4. The monomer of claim 3 wherein each R is methyl.

5. The monomer of claim 4 wherein each R is attached to the 3, 4, 7 or 8 carbon atom.

6. The monomer of claim 5 wherein there is a mixture of isomers wherein R groups are attached to different carbon atoms of the nonane ring.

7. The monomer of claim 5 wherein the monomer is a liquid at room temperature.

8. Monomer units of the formula:

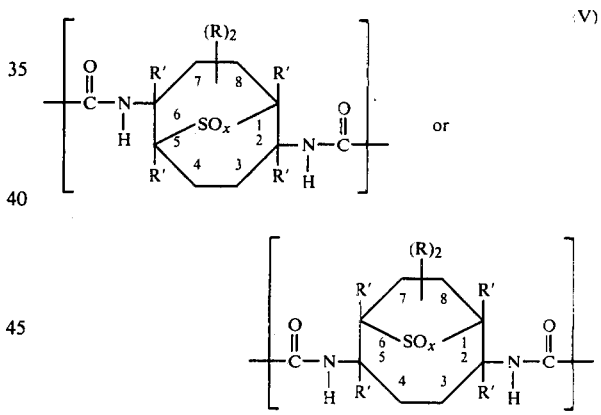

wherein each R, which may be the same or different, is an alkyl group containing 1 to 3 carbon atoms; each R', which may be the same or different, is hydrogen or methyl, at least two R' are hydrogen; and x is 0, 1 or 2.

9. Monomer units of claim 8 wherein all R' are hydrogen.

10. Monomer units of claim 9 wherein x is zero.

11. Monomer units of claim 10 wherein each R is methyl.

12. Monomer units of claim 11 wherein each R is attached to the 3, 4, 7 or 8 carbon atom.

13. Monomer units of claim 12 wherein there is a mixture of isomers wherein R groups are attached to different carbon atoms in different nonane rings.

14. Monomer units of claim 12 wherein the monomer is a liquid at room temperature.

15. A polymer containing a characterizing amount of the monomer units:

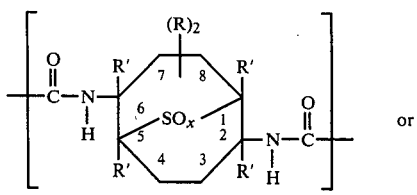

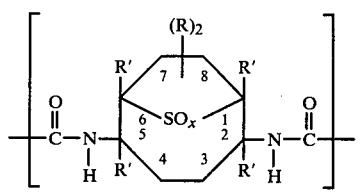

wherein each R, which may be the same or different, is an alkyl group containing 1 to 3 carbon atoms; each R', which may be the same or different, is hydrogen or methyl, at least two R' are hydrogens; and x is 0, 1 or 2.

16. The polymer of claim 15 wherein all R' are hydrogen.

17. The polymer of claim 16 wherein x is zero.

18. The polymer of claim 17 wherein each R is methyl.

19. The polymer of claim 18 wherein each R is attached to the 3, 4, 7 or 8 carbon atom.

20. The polymer of claim 19 wherein there is a mixture of isomers wherein R groups are attached to different carbon atoms in different nonane rings.

21. The polymer of claim 19 wherein the monomer is a liquid at room temperature.

22. The polymer of claim 15 wherein at least about 0.5 mole percent of the monomer units is present.

23. The polymer of claim 22 wherein at least about 10 mole percent of the monomer units is present.

24. The polymer of claim 23 wherein at least about 40 mole percent of the monomer units is present.

25. The polymer of claim 15 wherein the polymer is a polyurea, a polyurethane or a polyisocyanurate.

26. A method of forming a polymer comprising reacting a monomer of the formula:

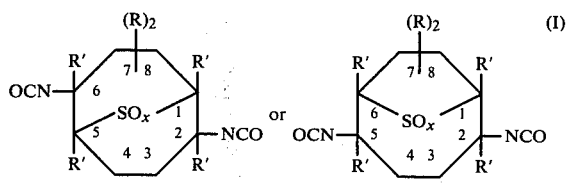

wherein each R, which may be the same or different, is an alkyl group containing 1 to 3 carbon atoms; each R', which may be the same or different, is hydrogen or methyl, at least two R' are hydrogens,; and x is 0, 1 or 2; with a polyol, a polyamine, a polybasic acid or an amino-alcohol to form the polymer which is a reaction product of said monomers and the polyol, polyamine, polybasic acid or amino-alcohol, respectively.

27. The method of claim 26 wherein all R' are hydrogen.

28. The method of claim 27 wherein x is zero.

29. The method of claim 28 wherein each R is methyl.

30. The method of claim 29 wherein each R is attached to the 3, 4, 7 or 8 carbon atoms.

31. The method of claim 30 wherein there is a mixture of isomers wherein R groups are attached to different carbon atoms in different nonane rings.

32. The method of claim 30 wherein the monomer is a liquid at room temperature.

* * * * *

UNITED STATES PATENT AND TRADEMARK OFFICE
CERTIFICATE OF CORRECTION

PATENT NO. : 4,458,061

DATED : July 3, 1984

INVENTOR(S) : David W. Hughes

It is certified that error appears in the above-identified patent and that said Letters Patent are hereby corrected as shown below:

Column 2, line 61, "R" should read -- R' --

Column 8, line 18, Claim 1, "x0," should read -- x is 0, --

Column 10, line 31, Claim 30, "atoms." should read -- atom. --

Signed and Sealed this

Twenty-second Day of January 1985

[SEAL]

Attest:

DONALD J. QUIGG

Attesting Officer     Acting Commissioner of Patents and Trademarks